US008821791B2

(12) United States Patent
Shibata et al.

(10) Patent No.: US 8,821,791 B2
(45) Date of Patent: *Sep. 2, 2014

(54) MONITORING METHOD, MONITORING APPARATUS AND LIQUID SAMPLE ANALYZER

(75) Inventors: Masaharu Shibata, Kobe (JP); Yoichi Nakamura, Kobe (JP)

(73) Assignee: Sysmex Corporation, Kobe (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/556,703

(22) Filed: Jul. 24, 2012

(65) Prior Publication Data

US 2012/0288407 A1 Nov. 15, 2012

Related U.S. Application Data

(63) Continuation of application No. 11/510,960, filed on Aug. 28, 2006, now Pat. No. 8,252,235.

(30) Foreign Application Priority Data

Aug. 29, 2005 (JP) ................................ 2005-248091

(51) Int. Cl.
*G01N 21/00* (2006.01)
*G01N 31/00* (2006.01)
*G01N 33/00* (2006.01)
*B01L 3/02* (2006.01)
*G01N 35/10* (2006.01)

(52) U.S. Cl.
USPC ................ 422/67; 422/63; 422/73; 422/514; 422/515; 73/864.24

(58) Field of Classification Search
USPC ................................ 422/67, 73, 63, 100, 102
See application file for complete search history.

(56) References Cited

U.S. PATENT DOCUMENTS

| 4,457,184 | A | 7/1984 | Shiono |
| 5,969,272 | A | 10/1999 | Tanaka |
| 6,281,517 | B1 | 8/2001 | Burkhardt et al. |
| 6,461,808 | B1 * | 10/2002 | Bodner et al. ............ 435/4 |
| 6,784,981 | B1 | 8/2004 | Roche et al. |
| 8,252,235 | B2 * | 8/2012 | Shibata et al. ............ 422/67 |
| 2003/0070498 | A1 * | 4/2003 | Ohyama et al. .......... 73/863.01 |
| 2005/0053521 | A1 * | 3/2005 | Hirayama ................ 422/67 |
| 2006/0039824 | A1 | 2/2006 | Onuma |

FOREIGN PATENT DOCUMENTS

| DE | 3302730 A1 | 8/1983 |
| EP | 0747689 A2 | 12/1996 |

(Continued)

OTHER PUBLICATIONS

European Search Report for European Application No. 06017881, dated Nov. 28, 2006, 2 pages.

*Primary Examiner* — Jill Warden
*Assistant Examiner* — Julie Tavares
(74) *Attorney, Agent, or Firm* — Brinks Gilson & Lione (57) ABSTRACT

A liquid sample is aspirated using an aspirating tube provided with a flow path extending lengthwise in the interior of the tube, and an aspiration orifice for aspirating the liquid sample formed near the tip of the tube. The aspiration of the liquid sample to the aspirating tube is monitored during aspiration. Liquid sample is aspirated by the aspirating tube, and the collected material in the aspirating tube in the region at the tip side from the region containing the liquid sample to be used for measurement is delivered to a detecting part provided externally to the aspirating tube, and whether or not liquid sample is contained in the collected material is detected in the detecting part.

14 Claims, 8 Drawing Sheets

(56) References Cited

FOREIGN PATENT DOCUMENTS

| | | | |
|---|---|---|---|
| EP | 0953843 | A2 | 11/1999 |
| EP | 0982593 | A1 | 3/2000 |
| EP | 1202066 | A2 | 5/2002 |
| EP | 1243929 | A1 | 9/2002 |
| JP | 59-065769 | A | 4/1984 |
| JP | 62-163968 | A | 7/1987 |
| JP | 2000-321288 | A | 11/2000 |

* cited by examiner

MONITORING METHOD, MONITORING APPARATUS AND LIQUID SAMPLE ANALYZER

This application is a continuation of U.S. application Ser. No. 11/510,960, filed Aug. 28, 2006 now U.S. Pat. No. 8,252,235, which claims priority under 35 U.S.C. §119 to Japanese Patent Application No. JP2005-248091 filed Aug. 29, 2005, the entire contents of each of which is hereby incorporated by reference.

FIELD OF INVENTION

The present invention relates to a monitoring method for monitoring an aspiration of a liquid sample, monitoring apparatus for monitoring an aspiration of a liquid sample, and a liquid sample analyzer.

BACKGROUND

Liquid sample analyzers for analyzing liquid samples such as blood and urine are widely known. Such liquid sample analyzers have a sample aspirating part (pipette) for aspirating a liquid sample in a container, and analyze the aspirated liquid sample via an analyzing part. Furthermore, such liquid sample analyzers have a function of monitoring whether or not a sample is aspirated normally.

Japanese Laid-Open Patent Publication No. 59-65769 discloses this type of sample aspirating apparatus. The sample aspirating apparatus disclosed in Japanese Laid-Open Patent Publication No. 59-65769 is provided with a first liquid sensor and a second liquid sensor, respectively, on bilateral sides of a sampling valve for measuring the sample aspirated by a sample aspirating pipette, so as to monitor whether or not a sample has been aspirated normally by whether or not the first liquid sensor and second liquid sensor detect a sample.

Moreover, Japanese Laid-Open Patent Publication No. 62-163968 discloses a pipette for confirming a liquid amount wherein a light transmitting part and a light blocking part are alternatingly arranged at predetermined spacing along the lengthwise direction of the pipette. This pipette for confirming a liquid amount is formed of transparent material such as quartz glass, hard transparent glass or the like. The surface has aluminum foil or the like vacuum deposited at predetermined spacing along the lengthwise direction. When light is emitted from a light emitting element, the light crosses through the pipette so as to be transmitted therethrough. The amount of liquid is verified by the light receiving element receiving the light from the light emitting element.

The sample aspirating apparatus disclosed in the Japanese Laid-Open Patent Publication No. 59-65769 requires measuring a sample via a sampling valve, however. Although the sampling valve is suited for simultaneously measuring and dividing a sample into a plurality of aliquots, such a valve is expensive and a large amount of sample is not used for analysis (dead volume) due to the need for a flow path from the pipette to the sampling valve.

Furthermore, the pipette for confirming a liquid amount disclosed in the Japanese Laid-Open Patent Publication No. 62-163968 requires high precision in the processing of the pipette used to measure minute samples, and such precision processing is problematic inasmuch as the pipette is formed of glass material such as quartz glass, hard transparent glass or the like.

BRIEF SUMMARY

The scope of the present invention is defined solely by the appended claims, and is not affected to any degree by the statements within this summary.

The first aspect of the present invention relates to a monitoring method for monitoring an aspiration of a liquid sample comprising:

aspirating a liquid sample via an aspiration tube that comprises an internal flow path extending in a lengthwise direction and an aspiration orifice formed near the tip thereof for aspirating liquid sample;

delivering a collected material in the aspiration tube contained in the region at the tip side from the region for collecting the liquid sample used for measurement to a detecting part provided externally to the aspiration tube; and detecting within the detecting part whether or not the collected material in the third region comprises liquid sample.

The second aspect of the present invention relates to a monitoring apparatus for monitoring an aspiration of a liquid sample comprising:

a dispensing part comprising an aspiration tube having an aspiration orifice near a tip thereof for aspirating a liquid sample; and a detecting part;

wherein the dispensing part dispenses a collected material in a first region of the aspiration tube and a collected material in a second region of the aspiration tube between the first region and the tip; and wherein the detecting part detects whether or not the collected material in the second region comprises liquid sample.

The third aspect of the present invention relates to a liquid sample analyzer comprising:

a dispensing part comprising an aspiration tube having an aspiration orifice near a tip thereof for aspirating a liquid sample; and a detecting part; and an analyzing part;

wherein the dispensing part dispenses a collected material in a first region of the aspiration tube and a collected material in a second region of the aspiration tube between the first region and the tip;

wherein the detecting part detects whether or not the collected material in the second region comprises liquid sample; and wherein the analyzing part analyzes the collected material within the first region.

DETAILED DESCRIPTION OF THE PREFERRED EMBODIMENTS

An embodiment of the present invention is described below based on the drawings.

The monitoring method of this invention is suited for method for monitoring an aspiration of a sample by using a pipette, or an apparatus for same. This type apparatus aspirates a liquid sample using an aspirating tube 21 (FIG. 7) that has an internal flow path 25 that extends in the lengthwise direction, and an aspirating orifice 26 near the tip thereof for aspirating a liquid sample or air. This monitoring method monitors whether or not a predetermined amount of a liquid sample within the aspirating tube 21 has been aspirated. Although examples of liquid sample include blood and urine, the embodiments of the monitoring method, monitoring apparatus, and liquid sample analyzer of the present invention are described via an example using a blood analyzer which analyzes blood as the analysis object.

Figure 1:
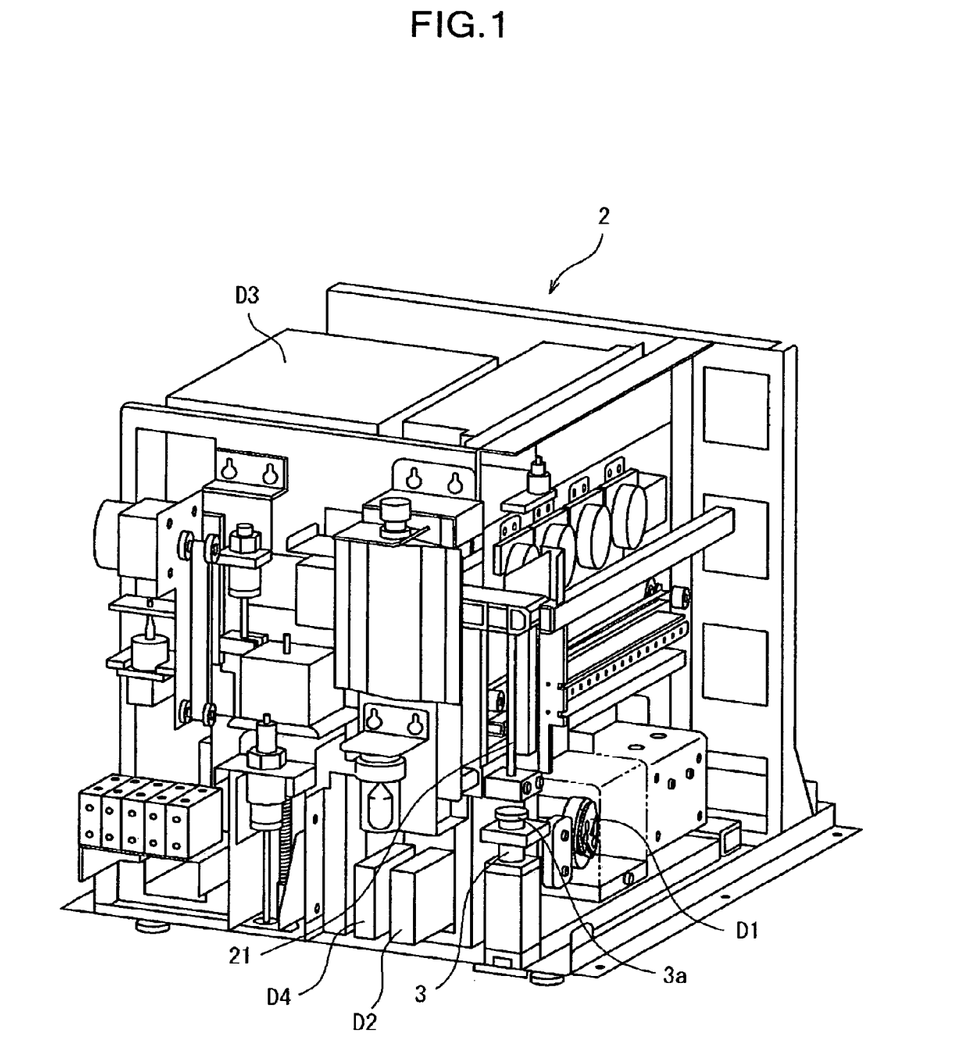
FIG. 1 is a perspective view of the blood analyzer including an embodiment of the monitoring apparatus for aspirating a liquid sample in which the external cover is removed.
Figure 2:
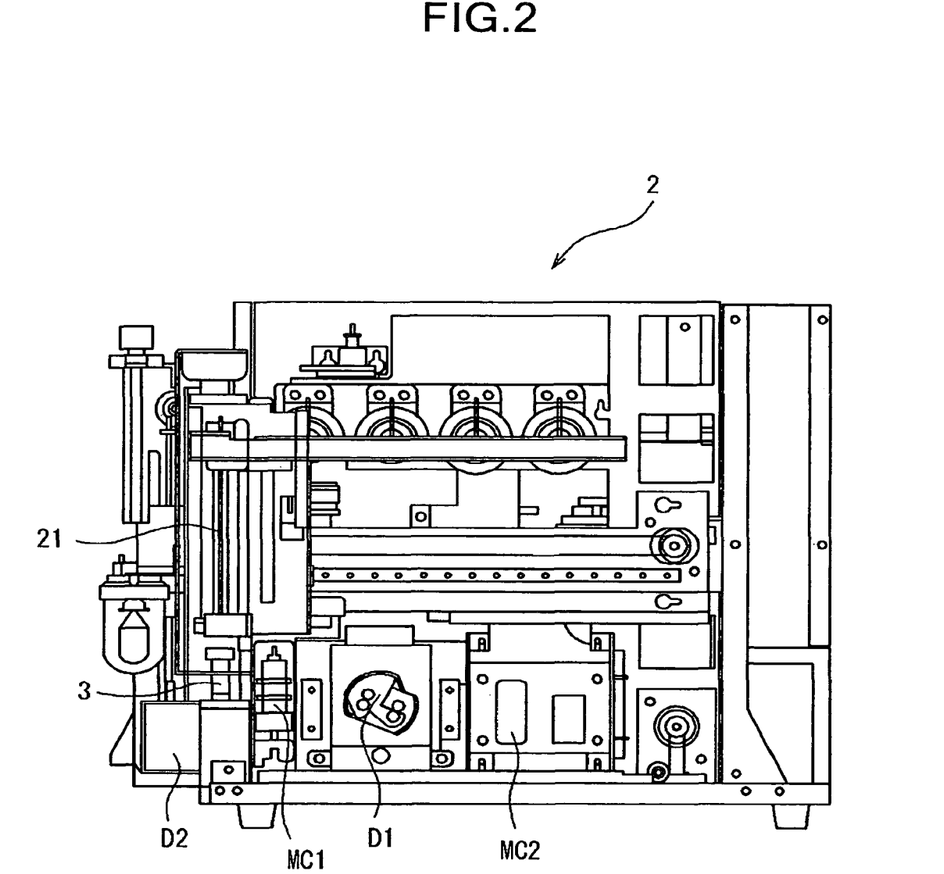
FIG. 2 is frontal view of the blood analyzer of FIG. 1.

FIG. 1 is a perspective view of the blood analyzer including an embodiment of the monitoring apparatus for aspirating a liquid sample in which the external cover is removed, and FIG. 2 is similarly a frontal view of the blood analyzer with the external cover removed.

The blood analyzer measures blood accommodated in a blood collecting tube 3, which is a sealed container (the initial collecting container of a sample), the mouth of which is sealed by a rubber plug 3a. The number of red blood cells and the like is measured automatically by simply setting the blood collecting tube 3 at a predetermined position. The blood analyzer is connected, in a manner so as to be capable of communicating, to a processing device (typically, a personal computer on which the required computer programs are installed) having a display, input device, CPU, memory and the like; this processing device has software installed thereon for implementing various types of settings for the monitoring of blood aspiration of the present invention, and the operation and analysis performed by the blood analyzer, display of analysis results and the like, such that the processing device is capable of communicating with the blood analyzer, issuing commands to the blood analyzer, and receiving measurement data from the blood analyzer.

The blood analyzer is provided with a sample setting part for setting the blood collecting tube 3 at a predetermined position in the apparatus, a sample preparing part for preparing an analysis sample by measuring and diluting a fixed amount of blood within the blood collecting tube 3, first detecting part D1, second detecting part D2, and third detecting part D3 for measuring (detecting) the blood that has been diluted and the like, and a controlling part for electrically controlling the actuation of the sample preparing part, and first through third detecting parts. The present embodiment of the blood analyzer further includes a fourth detecting part D4 for detecting optical information of a collecting material aspirated to the tip part (a second region on the tip side from a first region for collecting a liquid sample to be used for measurement) and/or the base part (a third region on the base side from the first region for collecting a liquid sample to be used for measurement) within the aspirating tube 21.

Figure 7:
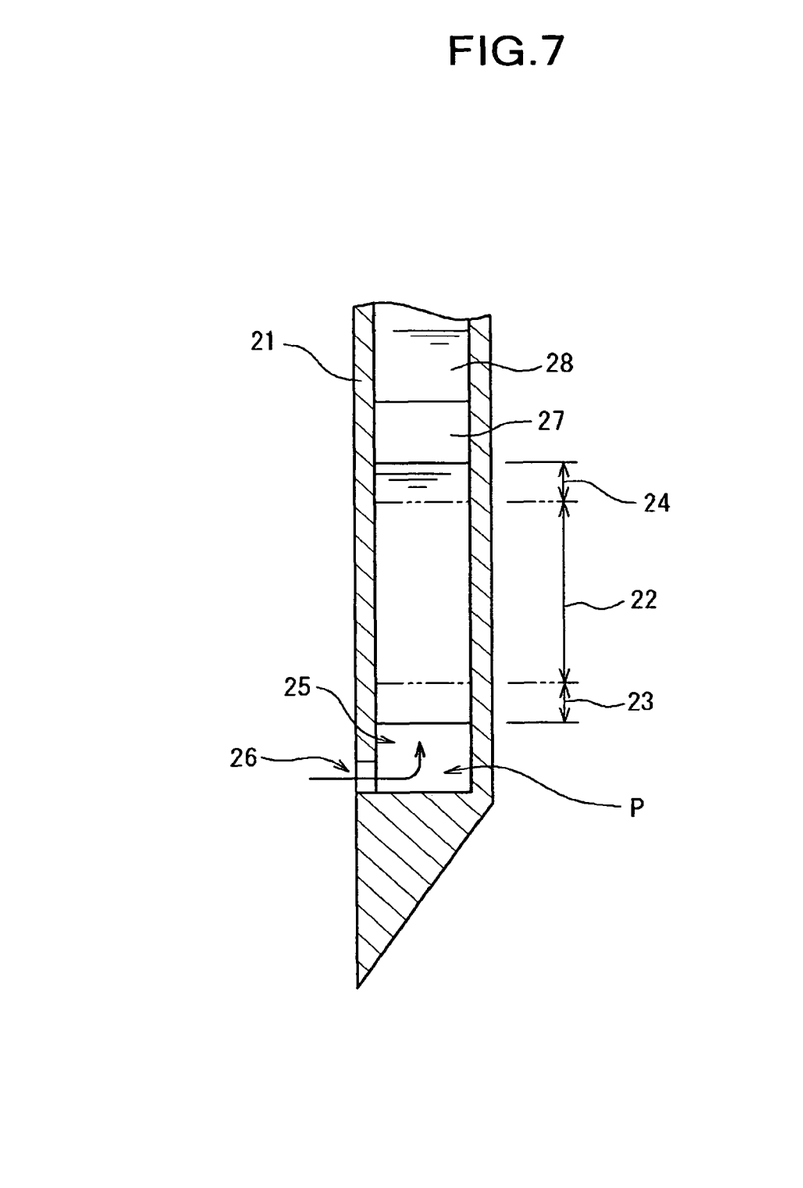
FIG. 7 is a sectional view of an embodiment of the aspirating tube.
Figure 8:
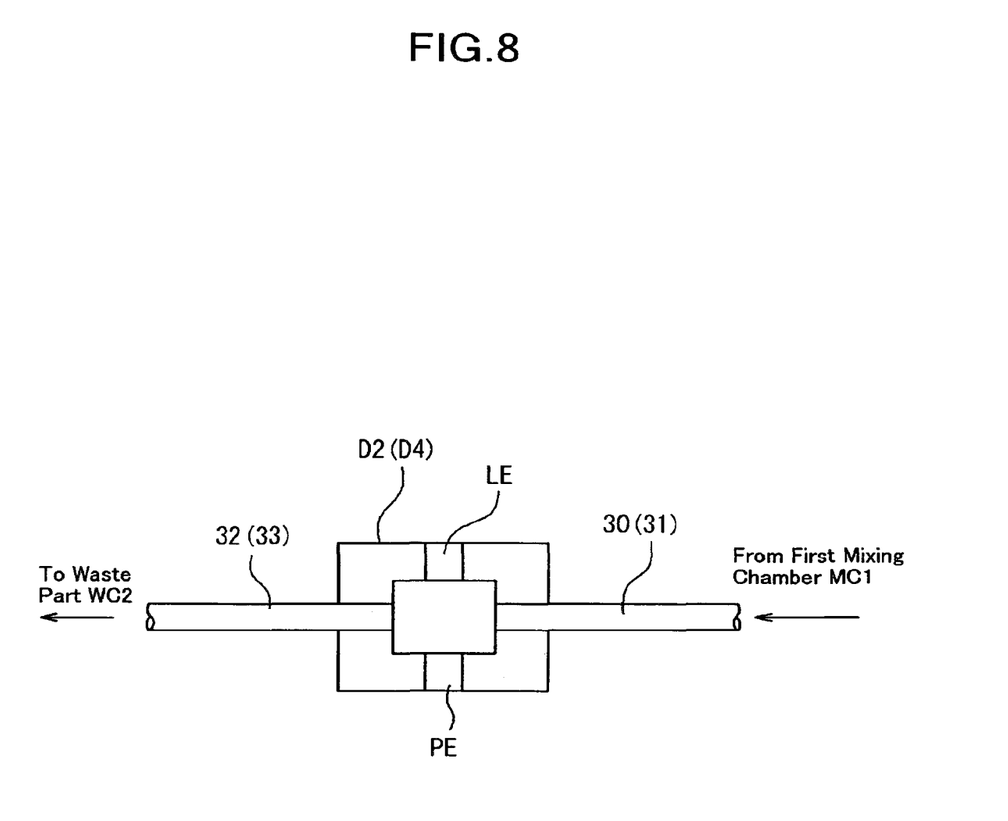
FIG. 8 illustrates an embodiment of the second (fourth) detecting part.

The aspirating tube 21 for aspirating blood within the blood collecting tube (sealed container) is made of a metal such as stainless steel alloy or the like, and has a sharp, needle-like tip, as shown in FIG. 7. A flow path P is formed to direct an aspirated sample to the interior of the aspirating tube 21. Therefore, the aspirating tube 21 is inserted through the stopper 3a, which is formed of rubber or the like, and seals the sealed container, and aspirates the sample collected in the sealed container. Since metal material is very strong and easily amenable to precision processing, the aspirating tube 21 can pierce the stopper 3a if the aspirating tube 21 has, for example, a very narrow shape with an internal diameter less than 1 mm. Moreover, a minute amount of sample can be measured by having the internal diameter of the aspirating tube 21 very narrow.

The first detecting part D1 can measure the number of red blood cells and number of platelets by a DC detection method. The first detecting part D1 has a flow cell, so as to supply a sample from a first mixing chamber MC1 (refer to FIG. 2) to the flow cell. When measuring red blood cells and platelets, a sample is prepared by mixing a diluting reagent with the blood in the first mixing chamber. This sample is supplied to the flow cell together with a sheath fluid, and forms a flow in which the sample is encapsulated by the sheath fluid within the flow cell. Furthermore, an aperture provided with an electrode is disposed within the flow path in the flow cell, such that the DC resistance at the aperture can be detected when the blood cells of the sample flow through the aperture one by one, and an electrical signal corresponding to this DC resistance is output. Since the DC resistance increases when the blood cell passes through the aperture, the electrical signal reflects the information relating to the blood cell passing through the aperture, and the number of red blood cells and platelets can be counted processing these electrical signals.

The second detecting part D2 and the fourth detecting part D4 are provided with a light emitting element LE such as an LED or the like, and a light receiving element PE such as a photodiode or the like. The second detecting part D2 and the fourth detecting part D4 are respectively connected to a tube 30 (31) extending from the first mixing chamber MC1, and communicate with the first mixing chamber MC1 through the tube 30 (31). Furthermore, the second detecting part D2 and the fourth detecting part D4 are respectively connected to a connecting tube 32 (33) of the waste part WC2 (refer to FIG. 3) which is used to dispose of the sample after it has been measured. In the second detecting part D2 and the fourth detecting part D4, the light emitting element LE and the light receiving element PE are arranged facing one another, and a mixed sample is supplied from the first mixing chamber MC1 and flows between the elements. Then, the light emitting element LE irradiates the mixed sample with light as the sample is supplied from the first mixing chamber MC1, and the opacity of the mixed sample is measured by the light receiving element PE receiving the light that passes through the mixed sample. The second detecting part D2 detects the hemoglobin concentration from the opacity, and the fourth detecting part D4 differentiates whether or not the measurement object is a sample based on the opacity.

The third detecting part D3 is an optical type flow cytometer capable of measuring white blood cells via a flow cytometric method using a semiconductor laser. The third detecting part D3 is provided with a flow cell for forming a sample flow. The flow cell is configured in a tube shape made of a material capable of transmitting light such as quartz, glass, synthetic resin and the like, and a flow path is formed in its interior through which the sample and sheath fluid flow. A sample prepared in a second mixing chamber MC2 (refer to FIG. 2) is introduced into the flow cell together with a sheath fluid, and a narrow flow is formed within the flow cell by the sample encapsulated in the sheath fluid. The third detecting part D3 includes a semiconductor laser light source, light receiving elements, and an optical unit having lenses and the like, such that when a sample flows through the flow cell, the sample is irradiated with laser light, and the optical signals of the fluorescent light and scattered light generated by the laser light are detected by the light receiving elements. The white blood cells contained in the sample are classified by predetermined classification criteria, or counted by processing the detection result.

FIGS. 3-6 shows the fluid circuit diagram of the blood analyzer of the present embodiment, with various types of containers and chambers arranged in the blood analyzer as shown in both drawings. Specifically, a first mixing chamber MC1 for preparing a mixed sample for measurements related to red blood cells, hemoglobin, and platelets, a second mixing chamber MC2 for preparing a mixed sample for measurements relating to white blood cells, a first detecting part D1 for measurements relating to red blood cells, a second detecting part D2 for measurements relating to hemoglobin, a third detecting part D3 for measurements relating to white blood cells, and a fourth detecting part D4 for detecting optical information of the collecting material aspirated to the tip part and/or the base part within the aspirating tube 21 are provided. Also provided are reagent vessels for accommodating reagents are diluting liquid vessel EPK-V for containing EPK diluting liquid (washing liquid), hemoglobin hemolytic reagent vessel SLS-V for containing hemoglobin hemolytic reagent SLS, white blood cell classifying hemolytic reagent vessel FFD-V for containing white blood cell hemolytic reagent FFD, and white blood cell classifying stain vessel FFS-V for containing white blood cell classifying stain FFS.

Figure 3:
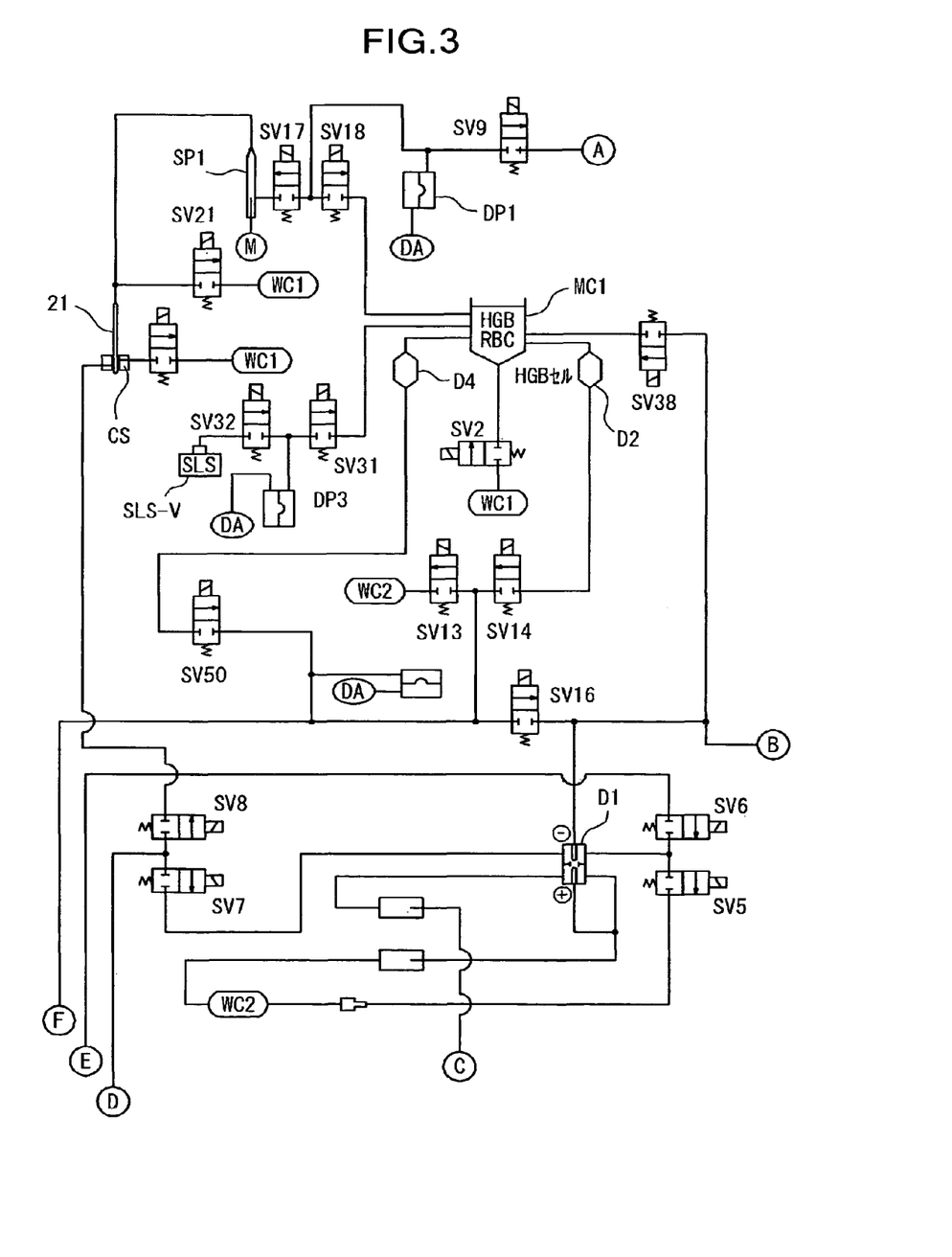
FIG. 3 shows the front half of an example of the flow circuit of a blood analyzer suited for this monitoring method.
Figure 4:
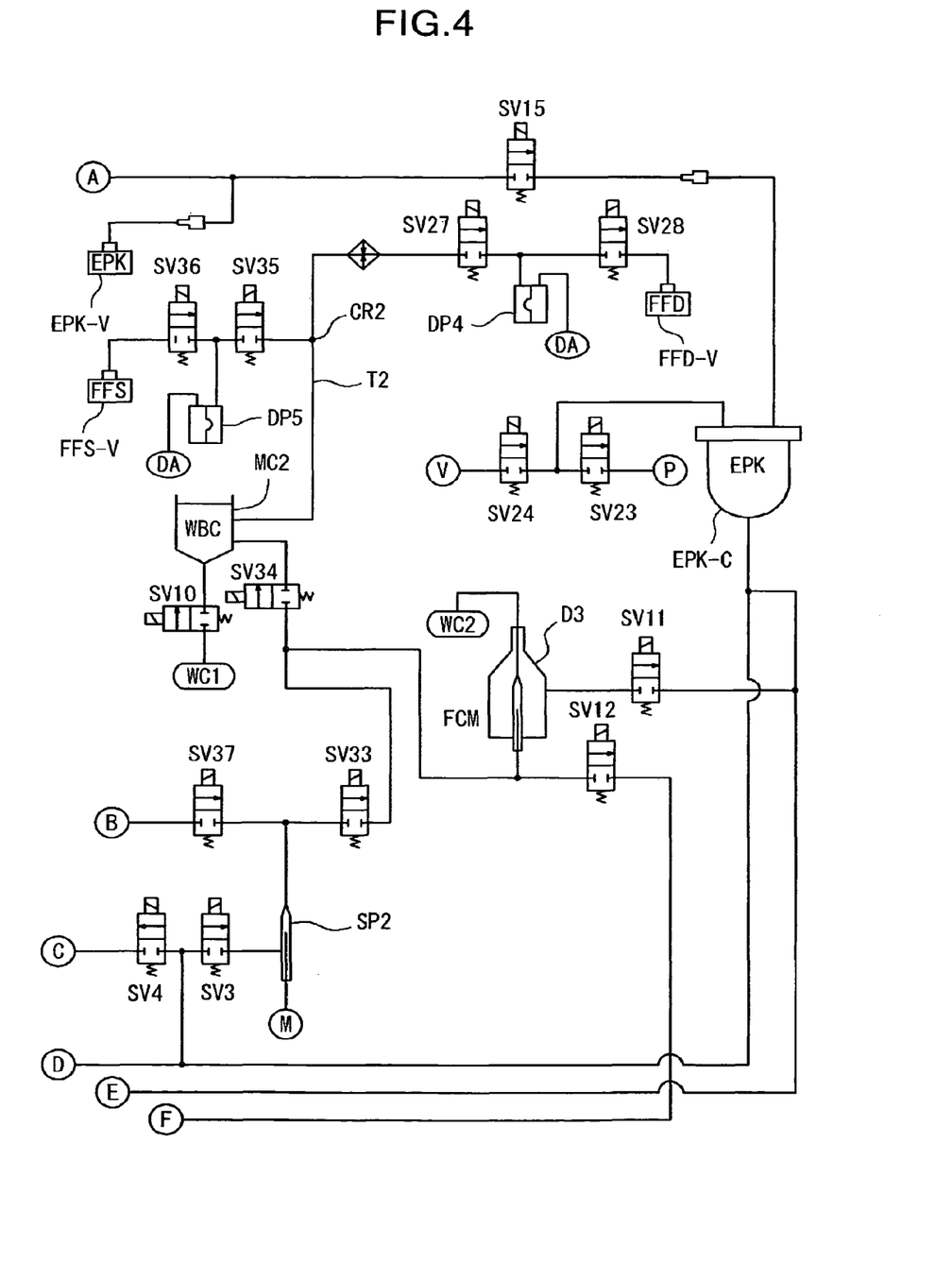
FIG. 4 shows the rear half of an example of the flow circuit of a blood analyzer suited for this monitoring method.
Figure 5:
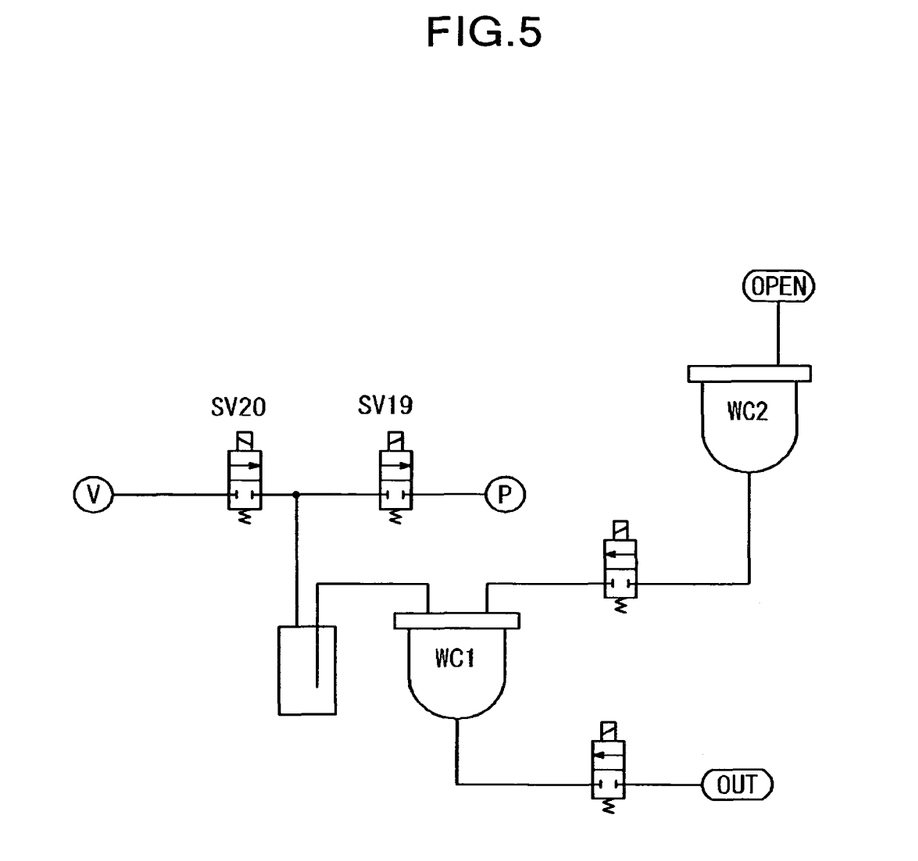
FIG. 5 shows the flow circuit on the periphery of the discharge liquid chamber.
Figure 6:
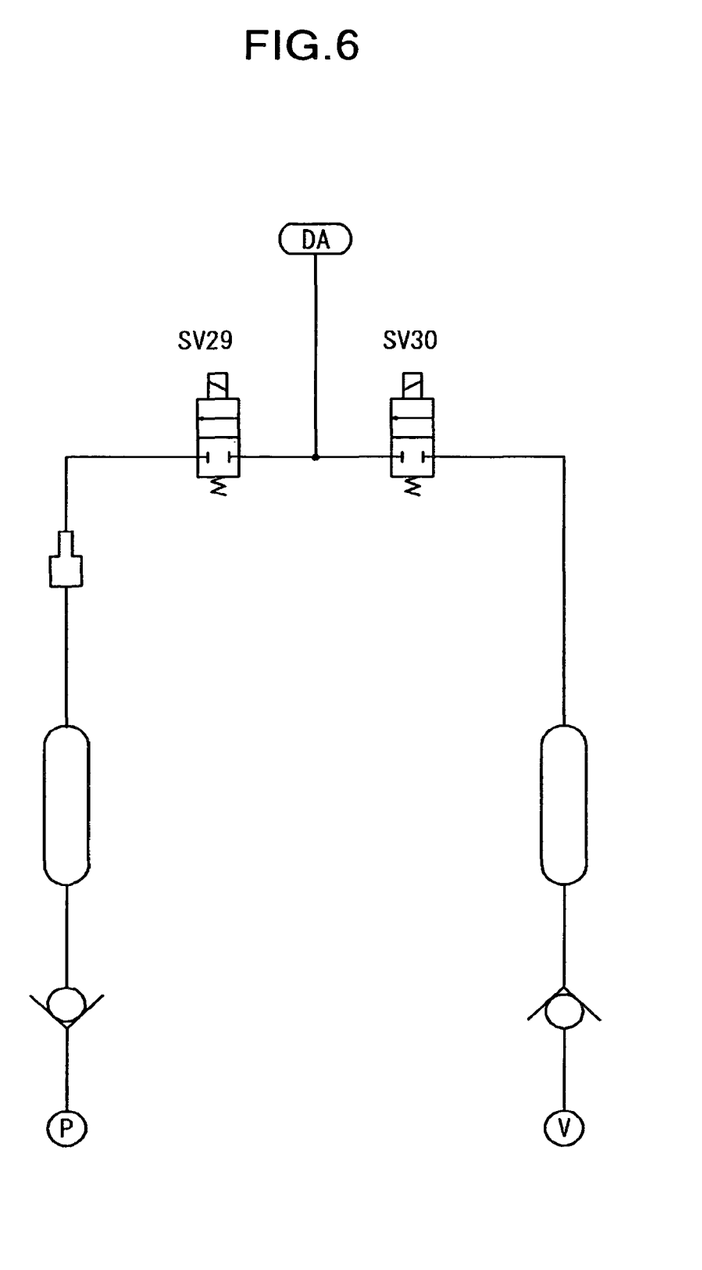
FIG. 6 shows the flow circuit on the periphery of the diaphragm pump.

Furthermore, the blood analyzer is provided with electromagnetic valves SV1-SV38, and SV-50 to open and close the flow paths (these electromagnetic valves are the normally closed type valves which are normally close), and various types of pumps and motors SP1-2 (syringe pumps for suctioning and supplying blood), P, V, DP1-5 (diaphragm pumps for measuring a liquid such as diluting liquid, hemolytic reagent, staining solution and the like) and the like, and these electromagnetic valves and the like are actuated and controlled by the controlling part. In FIG. 3, CS refers to a wash spitz for washing the aspirating tube.

The method for monitoring blood aspiration in the blood analyzer is described below.

(1) First, a set amount of blood is aspirated from the blood collecting tube 3 placed at a predetermined position in the apparatus using the aspirating tube 21. This aspiration is accomplished by the syringe pump SP1, which functions as a dispensing part (means for separately dispensing a collecting material in a first region for holding a liquid sample to be used for measurement, collecting material in a second region on the tip side from the first region, and collecting material in a third region on the base side from the first region). A "set amount" is an amount obtained by adding an amount used for monitoring aspiration to an amount (predetermined amount) used for actual measurement in the blood analyzer, and can be optionally set according to the blood measurement item, structure of the detecting part (mechanism for blood analysis) and the like. Specifically, when 15 µl is required as a measurement sample 22 (11 µl for WBC and 4 µl for RBC and HGB), then, if a monitoring amount of 2.5 µl is set for use in monitoring the respective measurement amounts of the measurement sample 22, the "set amount" becomes 20 µl, as shown in FIG. 7. The amount needed for monitoring aspiration should be sufficient to ensure the quantitative properties of the measurement sample, and should be less than the amount used for measurement. The sample used to monitor aspiration is aspirated in excess to accurately measure the measurement sample and is disposed of after this measurement whether or not aspiration monitoring is performed in the present embodiment, the sample used for aspiration monitoring is not consumed and wasting of the sample is suppressed.

In the present embodiment, a first part 23 of the collecting material in the second region on the tip side from the first region for containing the liquid sample to be used for measurement, and a second part 24 of the collecting material in the third region on the base side from the first region containing the liquid sample to be used for measurement, are both used for monitoring, the second part 24 of collecting material in the third region on the base side can be omitted. It is desirable that the monitoring sample parts 23 and 24 are set before and after the measurement sample 22; in this case, it is possible to monitor whether or not a predetermined amount of sample has been aspirated in the aspirating tube with greater accuracy by checking both the parts before and after the measurement part 22 actually used in analysis. That is, when the opacity of the before and after parts are measured and both opacities are greater than a predetermined value, the presence of a predetermined amount of sample in the part sandwiched between the before and after parts can be determined. In FIG. 7, reference numbers 27 and 28 respectively refer to an air gap and diluting solution.

(2) Next, the interior of the cell of the fourth detecting part D4 is washed using diluting solution.

(3) After the diluting solution has been discharged from the cell, diluting solution is supplied into the cell, and the opacity of the dilution solution is measured using the fourth detecting part D4. The fourth detecting part D4 is provided with, in addition to the cell, a light emitting element LE such as an LED or the like for emitting light for measurement, and a light receiving element PE such as a photodiode or the like for receiving the light emitted from the light emitting element LE that has been transmitted through the sample within the cell; the opacity of the sample is measured based on the difference in the amount of light emitted from the light emitting element E and the amount of light received by the light receiving element PE. After the measurement has been completed, the diluting solution is discharged from the cell once.

(4) Next, a mixed sample for monitoring is prepared by discharging 2.5 mL of blood of the first part to the first mixing chamber MC1 that has been supplied 1.0 mL of diluting solution, and delivering the mixed sample to the fourth detecting part D4, which measures the opacity of the mixed sample.

(5) After washing the first mixing chamber MC1, 4 mL of blood for RBC is discharged into the first mixing chamber MC1, which has been supplied 1.0 mL of diluting solution, to obtain a mixed sample for RBC measurement. Then, part of the mixed sample is delivered to the first detecting part D1, and measurement related to red blood cells is performed using a DC detection method.

(6) In parallel with the measurements related to red blood cells, 0.5 mL of white blood cell classifying hemolytic reagent is supplied to the second mixing chamber MC2, 11 µL of blood for WBC is discharged into the second mixing chamber MC2, 20 µL white blood cell classifying stain is supplied, and a mixed sample is obtained for WBC measurements. Then, the mixed sample is delivered to the third detecting part D3, and measurements related to white blood cells are performed via optical methods.

(7) a mixed sample is prepared for HGB by adding 0.25 mL of hemoglobin hemolytic reagent to 0.5 mL of the remaining mixed sample prepared for measurements related to white blood cells, and the obtained mixed sample is delivered to the second detecting part D2, and measurements related to hemoglobin are performed.

(8) After the first mixing chamber MC1 has been washed, 2.5 mL of blood of the second part 24 remaining in the aspirating tube 21 is discharged into the first mixing chamber MC1 to which 1.0 mL of diluting solution has been supplied, to obtain a mixed sample for monitoring, then the mixed sample is delivered to the fourth detecting part D4, and the opacity of the mixed sample is measured.

Whether or not blood is the measurement object in the first part 23 and second part 24 can be determined by comparing the opacity of the diluting solution and the respective opacities of the first part 23 and second part 24. For example, the first part 23 and second part 24 can be determined to be blood when the difference in the opacity of the dilution solution and the respective opacities of the first part 23 and second part 24 are greater than a fixed value (this value must be set beforehand by setting both the opacity of blood and the opacity of the diluting solution beforehand). Alternatively, a ratio may be used as a determination standard instead of the difference in opacities.

When the first part 23 and second part 24 used for monitoring have been determined to be a blood measurement object, it can be determined that a predetermined amount of blood needed for measurement exists between those two parts. Thus, analysis and the like based on blood of insufficient quantity can be avoided, and analysis precision and reliability can be improved by monitoring blood aspiration.

Furthermore, blood analysis can be stopped when it has been determined that the predetermined amount of blood has not been aspirated. Thus, the reagent and the like required for analysis is not wastefully used and the analyzer is used more efficiently by stopping an unnecessary analysis. The main causes of failure to aspirate a predetermined amount of blood are an insufficient amount of blood within the blood collecting tube (short sample), blood coagulation, and foreign matter present in the blood. More specifically, there is a high probability of having a short sample when there is no blood in the first part 23 at the terminal part of the tip end of the aspirating tube 21, and there is likewise a high probability that foreign matter may clog the aspirating tube when there is no blood in the second part 24 at the terminal part of the base end of the aspirating tube 21.

An error message may be generated when it has been determined that a predetermined amount of blood has not been aspirated. The technician performing the analysis is thus alerted to the blood aspiration problem by the generated error message. Therefore, the technician can take prompt countermeasures to inspect the analyzer and request that another blood sample be collected.

The embodiment described above monitors the aspiration of a liquid sample without the sampling valve used in the conventional art, thus reducing costs, by means of monitoring the aspiration of the liquid sample to the aspirating tube 21 by respectively delivering a collecting material in the aspiration tube 21 contained in a second region (first part 23) at the tip side from a first region for accommodating a liquid sample used for measurement and a collecting material in the aspiration tube 21 contained in a third region (second part 24) at the base side from the first region for accommodating the liquid sample used for measurement to the fourth detecting part D4 provided externally to the aspiration tube 21, and detecting in the fourth detecting part D4 whether or not a liquid sample is contained in the collecting material. Moreover, a metal pipette that is easily precision processed can be used to ensure aspiration accuracy at a low cost.

High viscosity liquids such as blood and the like reduce the fixed quantity precision at both ends (the aspiration starting part and the aspiration ending part when aspirated by the aspirating tube 21. Accordingly, when a sample in excess of that required for measurement is aspirated, the parts at bilateral ends used to ensure the fixed amount are normally discarded after having been aspirated. Particularly the aspiration ending part, that is, tip of the aspirating tube 21, has low aspiration accuracy. When a small amount of liquid sample is aspirated, the required amount of liquid sample can not be aspirated, and air is aspirated in the aspiration ending part (short sample). Accordingly, it is possible to monitor whether or not a short sample is produced, and thereby increase measurement accuracy, by detecting whether or not a liquid sample is included in the collecting material (first part 23) within the region at the tip of the aspirating tube 21.

Furthermore, insufficient aspiration of a sample may occur when the aspirating tube 21 becomes clogged with foreign matter; in this case the sample is not adequately aspirated and sample does not fill the aspirating tube 21 to the aspiration starting part, that is, the third region at the base end in the aspirating tube 21. However, this kind of aspiration insufficiency can be monitored by detecting whether or not liquid sample is contained in the collecting material (second part 24) in the third region at the base end in the aspirating tube 21, as in the present embodiment.

Since the first part 23 and second part 24 which are used to monitor the aspiration of the sample are wasted parts of the aspirated sample in the conventional art, the present embodiment does not require an excess of sample for monitoring aspiration of the sample, and does not increase the dead volume. That is, the wasted sample of the conventional art is used efficiently.

Although whether or not liquid sample is contained in the first part 23 and second part 24 is detected by detecting the optical information of opacity of the first part 23 and second part 24 in the present embodiment, when the sample has a low transparency as in the case of blood, whether or not there is sample in the first part 23 and second part 24 can be readily discriminated by the optical information since optical information such as opacity in this case will exhibit an obvious difference compared to air, such that monitoring aspiration of a sample can be accomplished simply.

In the present embodiment, an aspirating tube 21 pierces a blood collection tube 3 that contains a liquid sample and aspirates the liquid sample within the blood collection tube 3. The conventional art monitors the aspiration of the sample by measuring the aspiration pressure of the aspirating tube and monitoring the change in pressure. However, when the sample is sealed in a sealed container, accurately monitoring sample aspiration by measuring the pressure in the sealed container is problematic since the pressure change is unstable when the aspirating tube pierces the sealed container. Conversely, in the present embodiment, it is possible to accurately monitor aspiration even when aspirating a sample sealed in a sealed container since aspiration of the liquid sample to the aspirating tube 21 is monitored by measuring the opacity of the first part 23 at the tip of the aspirating tube 21 and the second part 24 at the base of the aspirating tube 21.

Although the present embodiment has been described in terms of a configuration having a fourth detecting part D4 for monitoring sample aspiration separate from the second detecting part D2 for measuring hemoglobin, the invention is not limited to this configuration inasmuch as the second detecting part D2 may be used for both measuring hemoglobin and monitoring sample aspiration. Furthermore, although the present embodiment has been described in terms of monitoring sample aspiration via the opacity of a mixed sample, the aspiration of a sample may also be accomplished by detecting other optical information such as light absorption, scattered light intensity and the like. Moreover, optical information such as opacity or the like may also be detected in samples containing not only dilution solution, but other reagents such as hemolytic reagent and the like.

Monitoring the aspiration of a sample may also be accomplished by counting red blood cells via a DC detection method using the first detecting part D1. Moreover, an electrode may be provided in the first mixing chamber MC1 so as to monitor sample aspiration by measuring electrical conductivity.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

The invention claimed is:

1. A liquid sample analyzer comprising:
a dispensing part comprising an aspiration tube having an aspiration orifice near a tip thereof for aspirating and discharging a liquid sample to be analyzed;
a measurement specimen preparing section comprising a chamber to mix a part of the liquid sample discharged from the aspiration tube and a reagent to prepare a measurement sample;
a detecting part comprising a light source and a light-receiving device;
an analyzing part configured to analyze the measurement sample prepared by the measurement specimen preparing section; and
a controller configured to:
cause the dispensing part to:
aspirate a first collected material in a first region of the aspiration tube, and a second collected material in a second region of the aspiration tube between the first region and the tip;
discharge the second collected material to the detecting part; and
discharge the first collected material into the chamber to prepare the measurement sample;
cause the detecting part to irradiate the second collected material discharged from the dispensing part with the light source and obtain optical information associated with the second collected material at the light-receiving device;
determine whether or not the first collected material is the liquid sample to be analyzed based on the optical information associated with the second collected material; and
output an alert responsive to a determination that the first collected material is not the liquid sample to be analyzed.

2. The liquid sample analyzer of claim 1, wherein the analyzing part and the detecting part are integrated.

3. The liquid sample analyzer of claim 1, wherein:
the detecting part is connected to the chamber through a first channel; and
the second collected material is discharged from the dispensing part into the chamber, then supplied from the chamber to the detecting part through the first channel.

4. The liquid sample analyzer of claim 3, wherein:
the analyzing part is connected to the chamber through a second channel; and
the first collected material is discharged from the dispensing part into the chamber, then supplied from the chamber to the analyzing part through the second channel.

5. The liquid sample analyzer of claim 1, wherein:
the dispensing part is configured to aspirate a third collected material in a third region of the aspiration tube between the first region and a base end of the aspiration tube;
the dispensing part is configured to discharge the third collected material after discharging the first collected material;
the detecting part is configured to receive the third collected material discharged by the dispensing part, irradiate the third collected material with the light source, and obtain optical information associated with the third collected material at the light-receiving device;
the controller is further configured to determine whether or not the first collected material is the liquid sample based on the optical information associated with the third collected material; and
the controller is further configured to output an alert responsive to a determination that the first collected material is not the liquid sample to be analyzed.

6. The liquid sample analyzer of claim 1, wherein the aspiration tube is configured so as to be insertable into a sealed container containing the liquid sample to be analyzed.

7. The liquid sample analyzer of claim 1, wherein the liquid sample to be analyzed comprises blood.

8. The liquid sample analyzer of claim 7, wherein the analyzing part is further configured to analyze hemoglobin in the measurement sample.

9. The liquid sample analyzer of claim 7, wherein the analyzing part is further configured to analyze blood cells in the measurement sample.

10. The liquid sample analyzer of claim 9, wherein the chamber is configured to mix the part of the sample with diluent so as to prepare the measurement sample for analyzing red blood cells in the measurement sample.

11. The liquid sample analyzer of claim 10, wherein the analyzing part is further configured to detect changes of DC resistance to count the red blood cells.

12. The liquid sample analyzer of claim 9, wherein the chamber is configured to mix the part of the sample with hemolytic reagent so as to prepare the measurement sample for analyzing white blood cells in the measurement sample.

13. The liquid sample analyzer of claim 12, wherein the analyzing part comprises an optical flow cytometer to count white blood cells.

14. A liquid sample analyzer comprising:
a dispensing part comprising an aspiration tube having an aspiration orifice near a tip thereof for aspirating and discharging a liquid sample to be analyzed;
a measurement specimen preparing section comprising a chamber to mix a part of the liquid sample discharged from the aspiration tube and a reagent to prepare a measurement sample;
a detecting part comprising a light source and a light-receiving device;
an analyzing part configured to analyze the measurement sample prepared by the measurement specimen preparing section; and
a controller configured to:
cause the dispensing part to:
aspirate a first collected material in a first region of the aspiration tube, and a second collected material in a second region of the aspiration tube between the first region and the tip;
discharge the second collected material to the detecting part; and
discharge the first collected material into the chamber to prepare the measurement sample;
cause the detecting part to irradiate the second collected material with the light source and obtain optical information associated with the second collected material at the light-receiving device;

determine whether or not the first collected material is the liquid sample to be analyzed based on the optical information associated with the second collected material;
cause the analyzing part to perform a measurement of the first collected material responsive to a determination that the first collected material is the liquid sample to be analyzed; and
output an alert responsive to a determination that the first collected material is not the liquid sample to be analyzed.

* * * * *